United States Patent [19]

George et al.

[11] 4,283,947
[45] Aug. 18, 1981

[54] SELF CLEANING, STEAM COOLED, GAS SAMPLE PROBE

[75] Inventors: David B. George; Leonard K. Bailey, both of Salt Lake City, Utah

[73] Assignee: Kennecott Copper Corporation, New York, N.Y.

[21] Appl. No.: 74,059

[22] Filed: Sep. 10, 1979

[51] Int. Cl.³ .............................................. G01N 1/22
[52] U.S. Cl. .................................................. 73/863.11
[58] Field of Search ..................... 73/421.5 R, 421.5 A

[56] References Cited

U.S. PATENT DOCUMENTS

| | | | |
|---|---|---|---|
| 3,011,336 | 12/1961 | Weiss | 73/421.5 R |
| 3,559,491 | 2/1971 | Thoen | 73/421.5 R |
| 3,938,390 | 2/1976 | Grey | 73/421.5 R |

FOREIGN PATENT DOCUMENTS 392374  12/1973  U.S.S.R. ............................ 73/421.5 R

Primary Examiner—Gerald Goldberg
Assistant Examiner—Denis E. Corr
Attorney, Agent, or Firm—Mallinckrodt & Mallinckrodt

[57] ABSTRACT

A gas sampling probe for industrial furnaces, such as reverberatory furnaces used in extractive metallurgy, is constructed with a sample tube concentrically disposed within a shield tube and spaced therefrom to provide an annular passage for a coolant fluid, such as steam or water vapor, which is discharged from the shield tube through ports therein located, for example, above the open lower end of the sample tube, as well as through the lower open end of such shield tube. The shield tube extends below the lower open end of the sample tube as a protection against accretion build-up, and an annular partition plate which is secured to the shield tube but terminates short of the sample tube permits free expansion and contraction of the sample tube while limiting discharge of the coolant fluid through the lower open end of the shield tube.

4 Claims, 2 Drawing Figures

SELF CLEANING, STEAM COOLED, GAS SAMPLE PROBE

BACKGROUND OF THE INVENTION

1. Field

The invention is in the field of gas sampling probes for industrial furnaces.

2. State of the Art

A variety of gas sampling probes for industrial furnaces have been developed in the past utilizing a fluid coolant for cooling purposes. However, there has been left considerable room for improvement from the standoints of effective operation and simplicity of construction. A structurally simple probe utilizing open-ended, concentric tubes is shown in Thoen U.S. Pat. No. 3,559,491 issued Feb. 2, 1971; the inner sampling tube or tubes are, however, made of a porous ceramic material, which results in a very expensive probe. Furthermore, it is sensitive to thermal changes and cannot be cooled. Moreover, such tubes must be flushed out periodically to remove accumulated particulate matter, so they won't become plugged.

3. Objectives

Principal objectives in the making of the present invention were to utilize an applied coolant fluid such as steam or water vapor as others had done, but with the structural simplicity of concentric tubes of a corrosion and heat resistant material such as stainless steel, with venting at the tip of the probe, and with a continuous cleaning action utilizing the coolant fluid as a cleaning agent.

SUMMARY OF THE INVENTION

In the accomplishment of the foregoing objectives, the gas sampling probe of the invention comprises a shield tube having an open end for placement within the furnace and a sample tube positioned concentrically within the shield tube and spaced therefrom to provide an annular passage for a coolant fluid. The sample tube terminates within the shield tube in an open end that is protectively surrounded by the open end portion of the shield tube, thereby shielding the tip of such sample tubes. To provide cleaning action by coolant fluid discharging from the probe into the interior of the furnace, an annular partition plate is provided between the two tubes adjacent to the open ends thereof so as to largely close the annular passage therebetween. Such partition plate is secured to the shield tube but terminates short of the sample tube, so as to permit free expansion and contraction of the latter and provide restricted passage for coolant fluid toward and past the open end of the sample tube to keep it clean. Ports for exhaust of a major amount of the coolant fluid are provided on the side of the shield tube away from the flow of furnace gas and on the side of the partition plate that is away from the open ends of the tubes. It is preferred that the probe be installed substantially vertically through the roof of the furnace, with the open ends of the tubes directed downwardly within the interior of the furnace and with means located exteriorly of the furnace for introducing a coolant fluid into the annular passage.

The probe of the invention is simpler in design than those of the prior art. It requires no moving parts, packing glands, nor exotic materials. These factors make for a very inexpensive, disposable probe. The use of single-pass steam cooling avoids the need for removal of hot coolant from the probe, which simplifies operation and eliminates dangers accompanying use of other coolants.

THE DRAWING

An embodiment of gas sampling probe representing the best mode presently contemplated for carrying out the invention is illustrated in the accompanying drawing wherein:

FIG. 1 is a central vertical section through the probe as installed through the roof of a reverberatory furnace; and FIG. 2, a horizontal section taken along the line 2—2 of FIG. 1 and drawn to a somewhat larger scale.

DETAILED DESCRIPTION OF ILLUSTRATED EMBODIMENT

Figure 1:
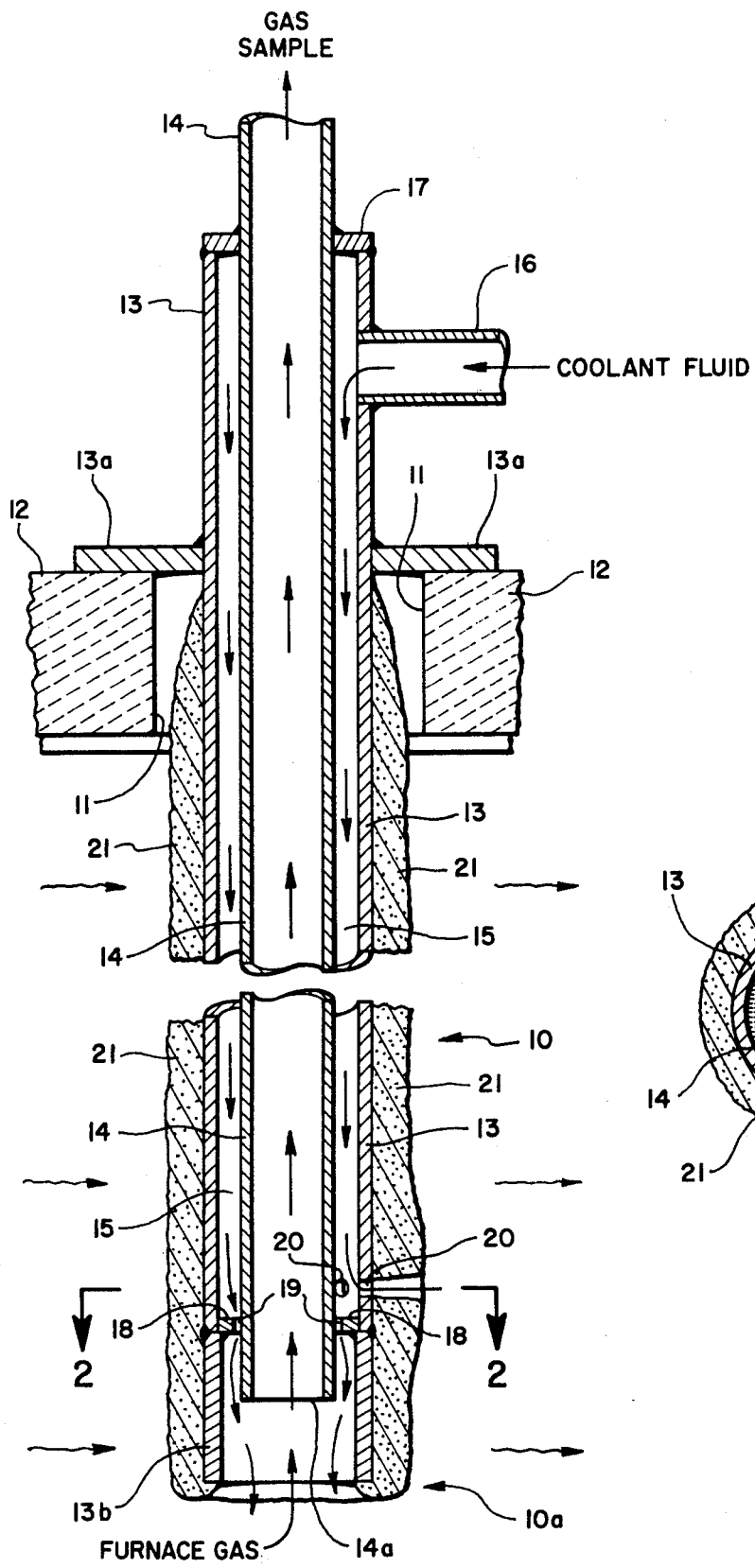
Figure 2:
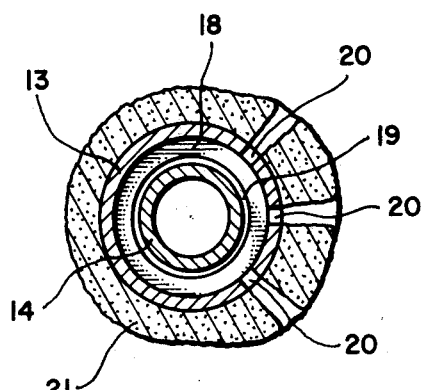

In the illustrated form of the invention, the probe indicated generally 10 is installed through a receiving opening 11 in the roof 12 of a reverberatory furnace, for example one used for smelting copper concentrates, which is illustrated only fragmentarily. The probe is disposed substantially vertically, with its intake end 10a positioned interiorly of the furnace and directed downwardly.

The probe 10 comprises a shield tube 13 and a sample tube 14 positioned concentrically within the shield tube and spaced therefrom to provide an annular passage 15 for a coolant fluid, which is introduced thereinto from any suitable source of same through a feed nipple 16 located near the upper end of the probe externally of the furnace. The upper end of shield tube 13 is capped at 17, and sample tube 14 extends through the capping to communicate with a receiver (not shown) for the sample gas removed from the interior atmosphere of the furnace.

It is preferred that the tubes 13 and 14 and the capping 17 be of stainless steel, so as to resist corrosion and withstand the furnace heat, although black iron construction has been used successfully. Any suitable mounting may be employed to hold the probe in position within roof opening 11, for example that shown at 13a as part of shield tube 13.

A typical probe will utilize two inch stainless steel pipe for the major length of shield tube 13 and one inch stainless steel pipe for sample tube 14. The lower end portion of the shield tube is preferably heavier gauge stainless steel than is the remainder of the tube, being welded in place through the intermediacy of an annular partition plate to be described.

The open intake end or tip 14a of sample tube 14 terminates within the open end portion 13b of shield tube 13, so as to be protectively surrounded by such portion 13b. Spaced backwardly from tip 14a of the sample tube and positioned between such sample tube and shield tube 13 is an annular partition plate 18.

Such plate 18 is secured to shield tube 13. In this illustrated instance, it is interposed between open end portion 13b of the shield tube and the remainder of the length thereof, and is welded to both. It terminates short of sample tube 14 to provide a restricted annular passage 19 about the outer circumference of such sample tube. Since there is no joinder of partition plate 18 to sample tube 14, the latter is free to expand and contract lengthwise relative to shield tube 13.

On the side of the partition plate which is away from the open ends of the tubes, that is to say upwardly of partition plate 18 in the present embodiment, shield tube 13 is provided with a substantially semi-circumferential series of ports, 20, for the discharge into the furnace atmosphere of a major amount of the coolant fluid flowing through the annular passage, 15, between the tubes. The probe is installed in the furnace so that ports 20 face away from the flow of furnace gas, which is normally at approximately right angles to the axis of the probe. A minor amount of such coolant fluid flows through the restricted annular passage, 19, to cool and clean the open end portion or tip, 14a, of the sample tube before discharging through open end portion 13b of the shield tube into the furnace atmosphere.

In operation, it has been found that a layer of slag 21 from about one-half inch to about two inches thick forms on the outer surface of shield tube 13, being thicker adjacent to the ports 20. This appears to have two beneficial effects, namely, prevention of corrosion of shield tube 13 and insulation of the probe, thereby reducing the extent of cooling required.

Although vertical positioning of the probe is preferred as illustrated, other suitable positioning may be utilized where appropriate.

It is again pointed out that the invention provides unique single-pass cooling by a probe having no moving parts and being capable of thermal expansion without requiring the use of packing glands. The probe is easily constructed, is easily installed and removed with respect to an industrial furnace, is relatively inexpensive to construct, and is disposable.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A gas sampling probe adapted for installation in an industrial furnace for removing sample portions of the gaseous atmosphere within such furnace, comprising a shield tube having an open end for placement within the furnace; a sample tube concentrically disposed within the shield tube and spaced therefrom to provide an annular passage for a coolant fluid, said sample tube terminating within the shield tube in an open end that is protectively surrounded by said shield tube; a partition plate extending across said annular passage between the shield tube and the sample tube adjacent to the open end of the latter, said partition plate being secured to the shield tube but terminating short of the sample tube, so as to permit free expansion and contraction of such sample tube and provide restricted passage for coolant fluid toward and past the open end of the sample tube to keep it clean; means for introducing a coolant fluid into said annular passge at or near the other end of the shield tube; port means at one side of the shield tube and at the side of the partition plate that is away from the open ends of the tubes, so as to discharge a major amount of the coolant fluid from the annular passage into a stream of furnace gas flowing past the probe; and means discharging sample gas from the sample tube at or near the other end thereof, so that the flow of that portion of the coolant fluid that passes by the partition plate in said annular passage is in substantially the opposite direction to the flow of said sample gas.

2. A gas sampling probe in accordance with claim 1, wherein the probe is adapted to be installed in a furnace in substantially vertical position with the open ends of the shield and sample tubes directed downwardly.

3. A gas sampling probe in accordance with claim 1, wherein the restricted passage for coolant fluid between the partition plate and the sample tube is an annulus whose gap is very narrow relative to the partition plate.

4. The combination of a gas sampling probe in accordance with claim 1 and an industrial furnace, the concentric tubes extending through a wall of the furnace.

* * * * *